US012105025B2

(12) United States Patent
Sasaki et al.

(10) Patent No.: US 12,105,025 B2
(45) Date of Patent: Oct. 1, 2024

(54) INSPECTION DEVICE FOR HYDRAULIC EQUIPMENT, INSPECTION SYSTEM FOR HYDRAULIC EQUIPMENT, WORK VEHICLE, AND INSPECTION METHOD FOR HYDRAULIC EQUIPMENT

(71) Applicant: KOMATSU LTD., Tokyo (JP)

(72) Inventors: Takatoshi Sasaki, Tokyo (JP); Masaya Kato, Tokyo (JP)

(73) Assignee: KOMATSU LTD., Tokyo (JP)

( * ) Notice: Subject to any disclaimer, the term of this patent is extended or adjusted under 35 U.S.C. 154(b) by 513 days.

(21) Appl. No.: 17/413,726

(22) PCT Filed: Mar. 10, 2020

(86) PCT No.: PCT/JP2020/010161
§ 371 (c)(1),
(2) Date: Jun. 14, 2021

(87) PCT Pub. No.: WO2020/195766
PCT Pub. Date: Oct. 1, 2020

(65) Prior Publication Data
US 2022/0050058 A1   Feb. 17, 2022

(30) Foreign Application Priority Data
Mar. 26, 2019   (JP) ................. 2019-059067

(51) Int. Cl.
*G01N 21/85*   (2006.01)
*E02F 9/22*   (2006.01)
(Continued)

(52) U.S. Cl.
CPC .......... *G01N 21/85* (2013.01); *E02F 9/2278* (2013.01); *E02F 9/26* (2013.01); *F15B 15/20* (2013.01);
(Continued)

(58) Field of Classification Search
CPC .... G01N 21/85; G01N 33/2841; G01N 21/94; E02F 9/2278; E02F 9/26; E02F 9/202;
(Continued)

(56) References Cited

U.S. PATENT DOCUMENTS

| | | | | |
|---|---|---|---|---|
| 5,239,861 A | * | 8/1993 | Fujita | ............ B01D 35/143 73/61.73 |
| 5,548,393 A | * | 8/1996 | Nozawa | ............ G01N 33/2888 359/507 |

(Continued)

FOREIGN PATENT DOCUMENTS

| | | | | |
|---|---|---|---|---|
| EP | 2864758 B1 | * | 4/2017 | ......... G01N 15/1031 |
| JP | 2010-7782 A | | 1/2010 | |

(Continued)

OTHER PUBLICATIONS

The International Search Report for the corresponding international application No. PCT/JP2020/010161, issued on May 26, 2020.

*Primary Examiner* — Mohamed K Amara
(74) *Attorney, Agent, or Firm* — Global IP Counselors, LLP

(57) ABSTRACT

An inspection device for hydraulic equipment includes a hydraulic circuit having a branch valve, an optical detection section, a pump configured to supply oil to the hydraulic circuit, and a controller. The optical detection section includes an inspection oil passage connected to the branch valve. The inspection oil passage includes a filter arranged to collect foreign matter. The controller operates the branch valve to supply oil to the inspection oil passage. The optical detection section includes first and second foreign matter detection sections arranged on upstream and downstream sides of the filter to detect foreign matter. A work vehicle includes the inspection device. An inspection system includes the inspection device. An inspection method includes supplying oil to an inspection oil passage by (Continued)

operating a branch valve of a hydraulic circuit, and detecting foreign matter on upstream and downstream sides of a filter arranged on the inspection oil passage.

13 Claims, 9 Drawing Sheets

(51) Int. Cl.
  *E02F 9/26* (2006.01)
  *F15B 15/20* (2006.01)
  *F15B 19/00* (2006.01)
  *G01N 33/28* (2006.01)
  *E02F 9/20* (2006.01)

(52) U.S. Cl.
  CPC ......... *F15B 19/00* (2013.01); *G01N 33/2841* (2013.01); *E02F 9/202* (2013.01)

(58) Field of Classification Search
  CPC ....... E02F 3/7618; E02F 9/2054; E02F 9/267; F15B 15/20; F15B 19/00; F15B 2211/611; F15B 2211/655; F15B 21/041; F15B 21/044
  See application file for complete search history.

(56) References Cited

U.S. PATENT DOCUMENTS

| | | | | |
|---|---|---|---|---|
| 6,081,324 | A  * | 6/2000 | Yagita | G01N 33/15 |
| | | | | 356/237.1 |
| 6,619,112 | B2 * | 9/2003 | Juhasz | B01D 46/44 |
| | | | | 73/865.9 |
| 8,812,267 | B2 * | 8/2014 | Satake | G01N 21/534 |
| | | | | 184/6.24 |
| 10,605,702 | B2 * | 3/2020 | Young | G01N 15/1404 |
| 2008/0262650 | A1 * | 10/2008 | Dorendorf | A01M 7/0092 |
| | | | | 700/240 |
| 2009/0229455 | A1 * | 9/2009 | Eichner | F04B 49/065 |
| | | | | 91/1 |
| 2011/0153275 | A1 | 6/2011 | Satake | |
| 2020/0232911 | A1 * | 7/2020 | Chikugo | G01N 21/27 |

FOREIGN PATENT DOCUMENTS

JP  3168161 U  6/2011
WO  2018/198498 A1  11/2018

* cited by examiner

INSPECTION DEVICE FOR HYDRAULIC EQUIPMENT, INSPECTION SYSTEM FOR HYDRAULIC EQUIPMENT, WORK VEHICLE, AND INSPECTION METHOD FOR HYDRAULIC EQUIPMENT

This application is a U.S. National stage application of International Application No. PCT/JP2020/010161, filed on Mar. 10, 2020. This U.S. National stage application claims priority under 35 U.S.C. § 119(a) to Japanese Patent Application No. 2019-059067, filed in Japan on Mar. 26, 2019, the entire contents of which are hereby incorporated herein by reference.

BACKGROUND

Field of the Invention

The present invention relates to an inspection device for a hydraulic equipment, an inspection system for a hydraulic equipment, a work vehicle, and an inspection method for a hydraulic equipment.

Background Information

Conventionally, work vehicles such as bulldozers and wheel loaders are provided with a hydraulic circuit that supplies lubricating oil to a power transmission device such as a transmission. A foreign matter such as metal wear debris may be mixed in such a hydraulic circuit, and the foreign matter mixed in oil is detected by a light-shielding detector (see, for example, Japanese Patent laid open No. 2010-7782).

SUMMARY

However, in the conventional configuration, when bubbles are mixed in the oil, the bubbles may be erroneously detected as foreign matters.

An object of the present invention is to provide an inspection device for a hydraulic equipment, an inspection system for a hydraulic equipment, a work vehicle and an inspection method for a hydraulic equipment capable of accurately inspecting a foreign matter mixed in a hydraulic circuit.

An inspection device for a hydraulic equipment according to the invention includes a hydraulic circuit, an optical detection section, a pump, and a controller. The hydraulic circuit includes a branch valve. The optical detection section is connected to the branch valve and includes an inspection oil passage having a filter for collecting a foreign matter. The pump supplies oil to the hydraulic circuit. The controller operates the branch valve to supply oil to the inspection oil passage. The optical detection section includes a first foreign matter detection section and a second foreign matter detection section. The first foreign matter detection section is arranged on an upstream side of the filter and detects a foreign matter. The second foreign matter detection section is arranged on a downstream side of the filter and detects a foreign matter.

An inspection method for a hydraulic equipment according to the invention includes an oil supply step and a foreign matter detection step. The oil supply step includes supplying oil to an inspection oil passage by operating a branch valve arranged on a hydraulic circuit. The foreign matter detection step includes detecting a foreign matter on both an upstream side and a downstream side of a filter arranged on the inspection oil passage.

According to the present invention, it is possible to provide an inspection device for a hydraulic equipment, an inspection system for a hydraulic equipment, a work vehicle, and an inspection method for a hydraulic equipment capable of accurately inspecting a foreign matter mixed in a hydraulic circuit.

DETAILED DESCRIPTION OF EMBODIMENT(S)

Hereinafter, embodiments according to the present invention will be described with reference to the drawings.

Embodiment 1

Configuration

Figure 1:
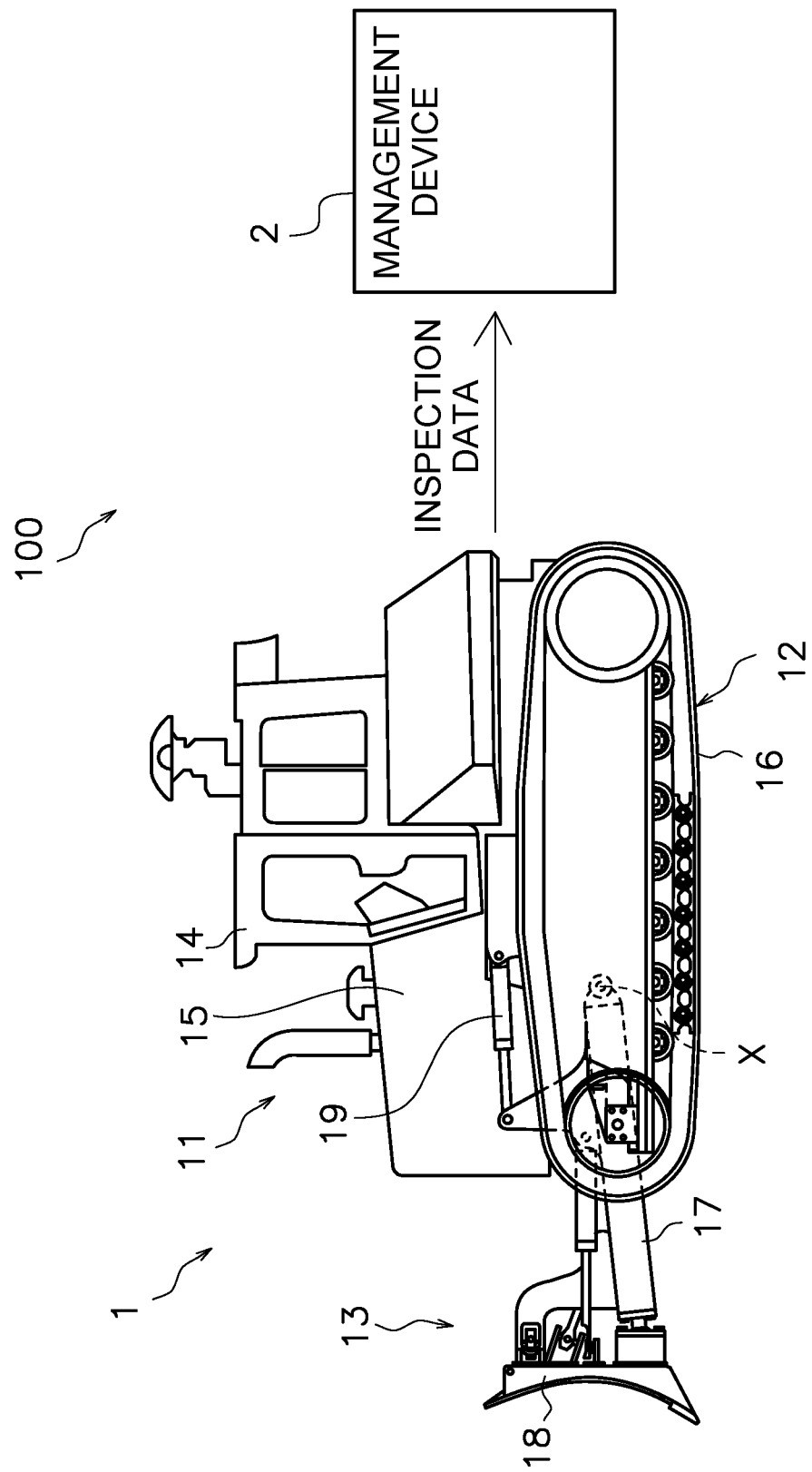
FIG. 1 is a view showing a work vehicle management system according to a first embodiment of the present invention.

FIG. 1 is a view showing a work vehicle management system 100 of the present embodiment. The work vehicle management system 100 of the present embodiment is a system that manages the work vehicle 1. The work vehicle management system 100 includes a work vehicle 1 and a management device 2. The work vehicle 1 transmits an inspection data of a hydraulic circuit to the management device 2. The management device 2 determines a state of the work vehicle 1 (occurrence of wear debris, occurrence of bubbles) based on the received inspection data.

FIG. 1 is a side view showing the work vehicle 1 of the present embodiment. The work vehicle 1 according to the present embodiment is a bulldozer. The work vehicle 1 includes a car body 11, a traveling device 12, a work implement 13, an inspection device 20 for a hydraulic equipment (see FIG. 2), and a receiver 27 (see FIG. 3).

Overview of Work Vehicle

The car body 11 includes a driver's cab 14 and an engine compartment 15. A driver's seat (not illustrated) is arranged in the driver's cab 14. The engine compartment 15 is arranged in front of the driver's cab 14. The traveling device 12 is attached to a lower part of the car body 11. The traveling device 12 includes a pair of left and right crawler belts 16. In FIG. 1, only the crawler belt 16 on the left side is illustrated. The work vehicle 1 travels by rotating the crawler belts 16.

The work implement 13 is attached to the car body 11. The work implement 13 includes a lift frame 17, a blade 18, and a lift cylinder 19.

The lift frame 17 is attached to the car body 11 so as to be movable up and down about an axis X extending in a car width direction. The lift frame 17 supports the blade 18. The blade 18 is arranged in front of the car body 11. The blade 18 moves up and down as the lift frame 17 moves up and down. The lift frame 17 may be attached to the traveling device 12.

The lift cylinder 19 is connected to the car body 11 and the lift frame 17. As the lift cylinder 19 expands and contracts, the lift frame 17 rotates up and down about the axis X.

Inspection Device for Hydraulic Equipment

Figure 2:
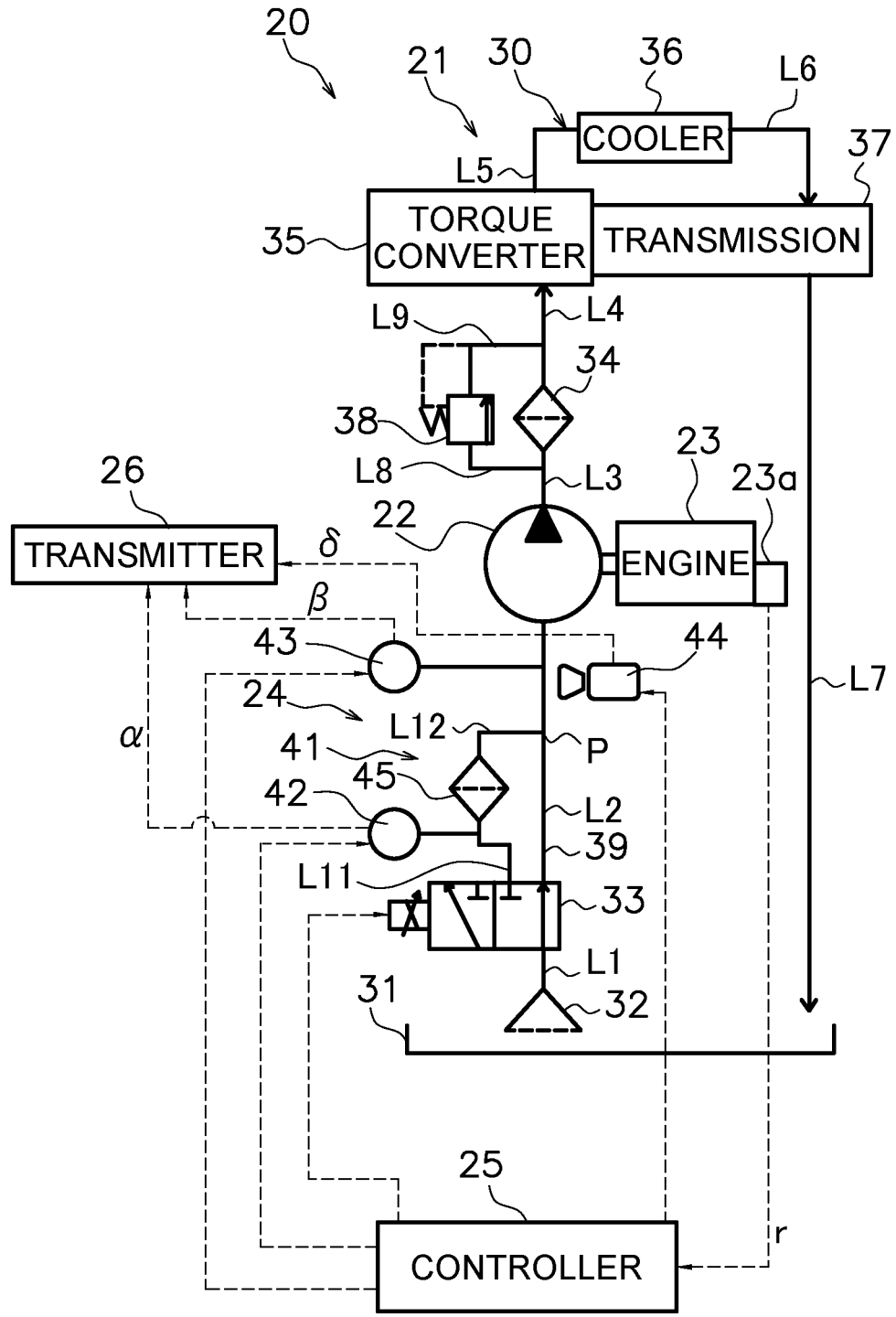
FIG. 2 is a view showing an inspection device for a hydraulic equipment included in the work vehicle in FIG. 1.
Figure 3:
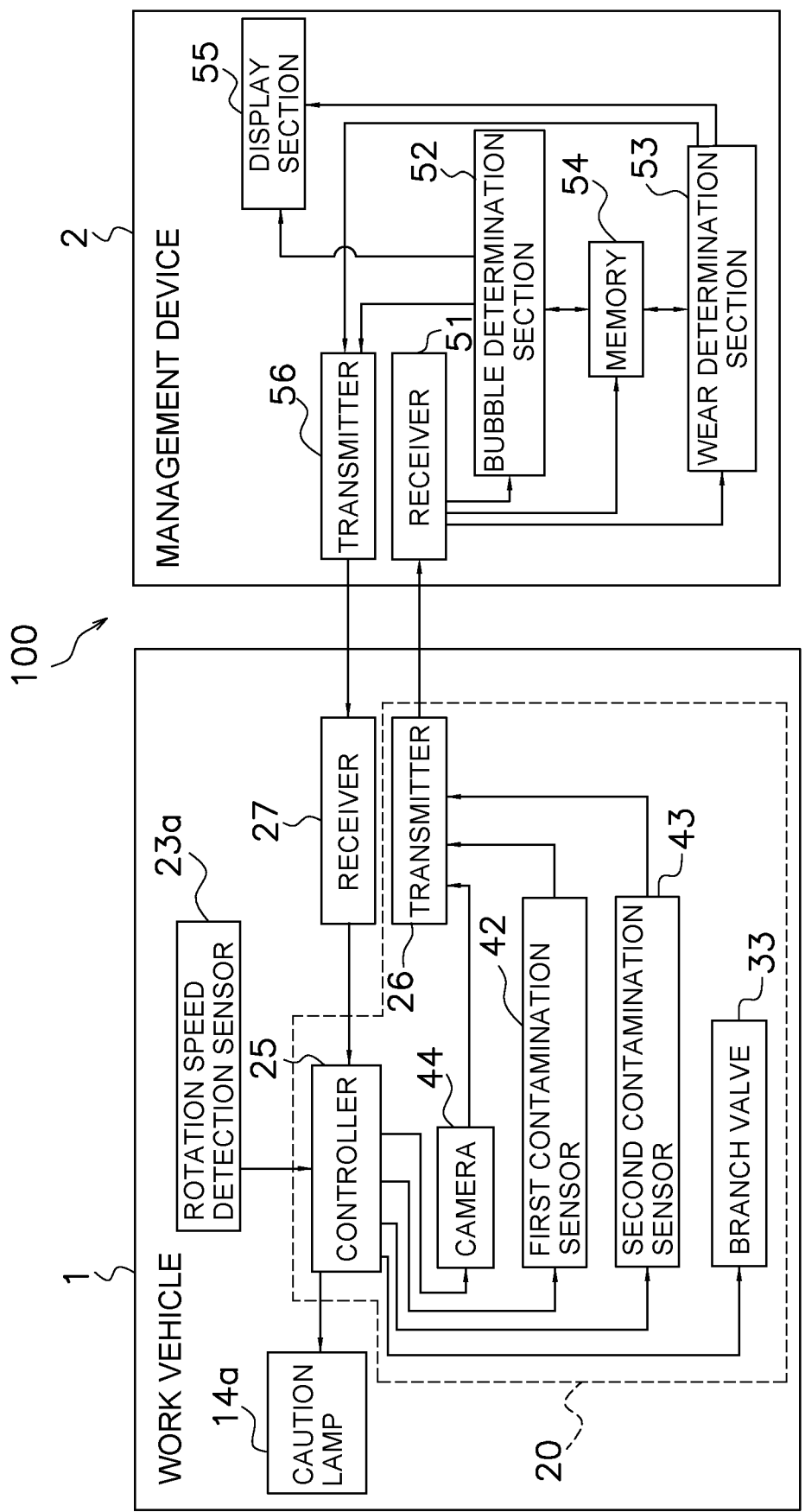
FIG. 3 is a block diagram showing a configuration of the work vehicle management system in FIG. 1.

FIG. 2 is a view showing a configuration of the inspection device 20 for the hydraulic equipment of work vehicle 1. FIG. 3 is a block diagram showing the configuration of the work vehicle management system 100.

The inspection device 20 for the hydraulic equipment of the present embodiment includes a hydraulic circuit 21, a hydraulic pump 22 (an example of a pump), an engine 23 (an example of a prime mover), an optical detection section 24, a controller 25, and a transmitter 26.

The hydraulic circuit 21 is provided to supply lubricating oil to a transmission 37 of work vehicle 1. The hydraulic pump 22 is connected to the hydraulic circuit 21, and supplies oil to the hydraulic circuit 21. The engine 23 drives the hydraulic pump 22. The optical detection section 24 optically detects wear debris. The controller 25 detects wear debris (an example of foreign matter) using the optical detection section 24 based on the rotation speed of the engine 23.

Hydraulic Circuit, Pump, and Engine

The hydraulic circuit 21 includes a lubricating oil tank 31, a suction filter 32, a branch valve 33, a lubricating oil filter 34, a torque converter 35, a cooler 36, a transmission 37, a relief valve 38, and pipelines L1 to L7.

In the present embodiment, the suction filter 32, the branch valve 33, and the pipelines L1 to L2 form a suction passage 39 for lubricating oil from the lubricating oil tank 31 to the hydraulic pump 22. Further, the pipelines L3 to L6, the lubricating oil filter 34, the torque converter 35 and the cooler 36 form an oil supply passage 30 for guiding the lubricating oil from the hydraulic pump 22 to the transmission 37. The oil pressure of the lubricating oil is maintained in the oil supply passage 30, and the pressure is applied to the lubricating oil flowing through the oil supply passage 30 by the hydraulic pump 22. In this way, the lubricating oil is supplied to the hydraulic circuit 21 by the hydraulic pump 22 connected to the hydraulic circuit 21.

The lubricating oil tank 31 stores the lubricating oil. The suction filter 32 is arranged in the lubricating oil stored in the lubricating oil tank 31. The suction filter 32 filters foreign matter (relatively large metal wear debris, etc.) mixed in the lubricating oil. The opening of the suction filter 32 can be set to a size that does not obstruct the flow of lubricating oil.

The branch valve 33 is connected to the suction filter 32 via the pipeline L1. The pipeline L1 is connected to the inlet port of the branch valve 33. The pipeline L2 and an inspection pipeline L11 (described later) are connected to the outlet port of the branch valve 33. The branch valve 33 is an electromagnetic valve, and switches the supply destination of the lubricating oil supplied from the pipeline L1 to the pipeline L2 or the inspection pipeline L11.

The hydraulic pump 22 is connected to the branch valve 33 via the pipeline L2. The hydraulic pump 22 is driven by the rotational driving force of the engine 23. The hydraulic pump 22 supplies lubricating oil to the oil supply passage 30. The hydraulic pump 22 sucks the lubricating oil from the lubricating oil tank 31 side through the suction passage 39, compresses the lubricating oil internally, and then discharges the lubricating oil to the lubricating oil filter 34 side. The lubricating oil discharged from the hydraulic pump 22 is guided to the transmission 37 through the oil supply passage 30. As the hydraulic pump 22, for example, a fixed displacement pump can be used.

The engine 23 drives the hydraulic pump 22. The driving force from the engine 23 is transmitted to the transmission 37 described later. A rotation speed detection sensor 23a for detecting the rotation speed of the engine 23 is provided, and the detected rotation speed r is transmitted to the controller 25 described later.

The lubricating oil filter 34 is connected to the hydraulic pump 22 via the pipeline L3. The lubricating oil filter 34 filters foreign matter (relatively small metal wear debris, etc.) mixed in the lubricating oil. The opening of the lubricating oil filter 34 may be smaller than the opening of the suction filter 32.

The torque converter 35 is connected to the lubricating oil filter 34 via the pipeline L4. The torque converter 35 transmits the rotational power from the engine 23 to the transmission 37.

The cooler 36 is connected to the torque converter 35 via the pipeline L5. The cooler 36 cools the lubricating oil heated in the torque converter 35. The cooler 36 cools the lubricating oil, for example, by receiving an air flow from a cooling fan.

The transmission 37 shifts the rotational power of the engine 23 transmitted from the torque converter 35 and transmits the driving force to the traveling device 12 illustrated in FIG. 1. The transmission 37 includes a forward gear corresponding to a forward traveling stage, a reverse gear corresponding to a reverse speed stage, and one or more speed stage gears corresponding to each speed stage. In the transmission 37, shifting is performed by selectively engaging each gear according to the traveling direction, the desired driving force, and the desired speed.

Lubricating oil is supplied to each gear of the transmission 37 from the pipeline L6. Lubricating oil is agitated by each gear. At the time of agitating, bubbles occur in the lubricating oil and the lubricating oil becomes cloudy. The cloudy lubricating oil is returned to the lubricating oil tank 31 via the pipeline L7.

Further, the relief valve 38 adjusts the pressure in the oil supply passage 30. The relief valve 38 is connected between the pipeline L8 branched from the pipeline L3 and the pipeline L9 joining the pipeline L4.

Optical Detection Section

The optical detection section 24 includes an inspection oil passage 41, a first contamination sensor 42 (an example of a first foreign matter detection section), a second contamination sensor 43 (an example of a second foreign matter detection section), and a camera 44 (an example of a bubble detection section).

The inspection oil passage 41 is connected to the outlet port of the branch valve 33 and joins the pipeline L2. The inspection oil passage 41 includes an inspection filter 45 (an example of a filter) and inspection pipelines L11 and L12. The inspection pipeline L11 is connected to the outlet port of the branch valve 33. The inspection filter 45 is connected to the branch valve 33 via the inspection pipeline L11. The inspection pipeline L12 connects the inspection filter 45 and the pipeline L2. The opening of the inspection filter 45 filters foreign matter (relatively small metal wear debris, etc.) mixed in the lubricating oil. The opening of the inspection filter 45 is smaller than the opening of the suction filter 32. The opening of the inspection filter 45 is large enough to allow bubbles mixed in the lubricating oil to pass through.

The first contamination sensor 42 detects foreign matter in the lubricating oil flowing through the inspection pipeline L11.

The second contamination sensor 43 detects foreign matter in the lubricating oil flowing through the pipeline L2 on the downstream side of the confluence point P with the inspection pipeline L12.

Each of the first contamination sensor 42 and the second contamination sensor 43 is an optical detector. Although not illustrated, each of the first contamination sensor 42 and the second contamination sensor 43 includes a light emitting component that emits light (for example, laser light) to the lubricating oil and a light receiving component to which light from the light emitting component is incident. The first contamination sensor 42 and the second contamination sensor 43 detect the wear debris amount in the lubricating oil based on the degree to which the emitted light is blocked by the wear debris in the lubricating oil. Specifically, the wear debris amount is detected by converting the rate of decrease in luminous intensity of the incident light on the light receiving component with respect to the light emitted from the light emitting component into a voltage. The wear debris amount $\alpha$ (an example of data relating to an amount of foreign matter) detected by the first contamination sensor 42 is transmitted to a transmitter 26 described later. Further, the wear debris amount $\beta$ (an example of data relating to an amount of foreign matter) detected by the second contamination sensor 43 is transmitted to the transmitter 26 described later.

The camera 44 captures the lubricating oil flowing through the pipeline L2 on the downstream side of the confluence point P with the inspection pipeline L12. The camera 44 may be, for example, a high-speed camera. Bubbles of lubricating oil are detected based on an image $\delta$ (an example of data relating to detection accuracy) taken by the camera 44. Specifically, the transparency of the lubricating oil is detected based on the image $\delta$ captured by the camera 44. When the transparency is lower than the predetermined threshold value, it is determined that the lubricating oil contains bubbles. The image $\delta$ captured by the camera 44 is transmitted to the controller 25.

When the rotation speed r of the engine 23 from the rotation speed detection sensor 23a becomes lower than the predetermined rotation speed, the controller 25 determines that the engine is at low rotation speed (idling), and sends a switching signal to the branch valve 33. As a result, the branch valve 33 is switched so as to connect the pipeline L1 and the inspection pipeline L11, and the lubricating oil flows into the inspection pipeline L11. The controller 25 can be executed by a processor such as a CPU (Central Processing Unit).

Further, the controller 25 transmits an operation signal to the first contamination sensor 42, the second contamination sensor 43, and the camera 44 after transmitting the switching signal to the branch valve 33.

As a result, the first contamination sensor 42 detects the wear debris amount $\alpha$, the second contamination sensor 43 detects the wear debris amount $\beta$, and the camera 44 captures the image $\delta$.

The transmitter 26 transmits the data of the wear debris amount $\alpha$, the wear debris amount $\beta$, and the image $\delta$ to the management device 2.

When the management device 2 determines that bubbles occur or wear occurs, the receiver 27 receives a signal indicating the determination result.

Upon receiving the signal indicating the determination result, the controller 25 turns on the caution lamp 14a provided in the driver's cab 14.

Management Device

As illustrated in FIG. 3, the management device 2 includes a receiver 51, a bubble determination section 52, a wear determination section 53, a memory 54, a display section 55, and a transmitter 56.

The receiver 51 receives the data of the wear debris amount $\alpha$, the wear debris amount $\beta$, and the image $\delta$ transmitted from the transmitter 26 in the work vehicle 1.

The bubble determination section 52 detects the transparency from the data of the image $\delta$, and when the detected transparency is lower than the predetermined threshold value, the bubble determination section 52 determines that bubbles occur.

The wear determination section 53 determines that wear occurs from the values of the wear debris amount $\alpha$ and the wear debris amount $\beta$. Specifically, the wear determination section 53 determines that wear occurs when the value of $\alpha/(\alpha+\beta)$ is equal to or greater than the predetermined threshold value $\gamma$.

Figure 4:
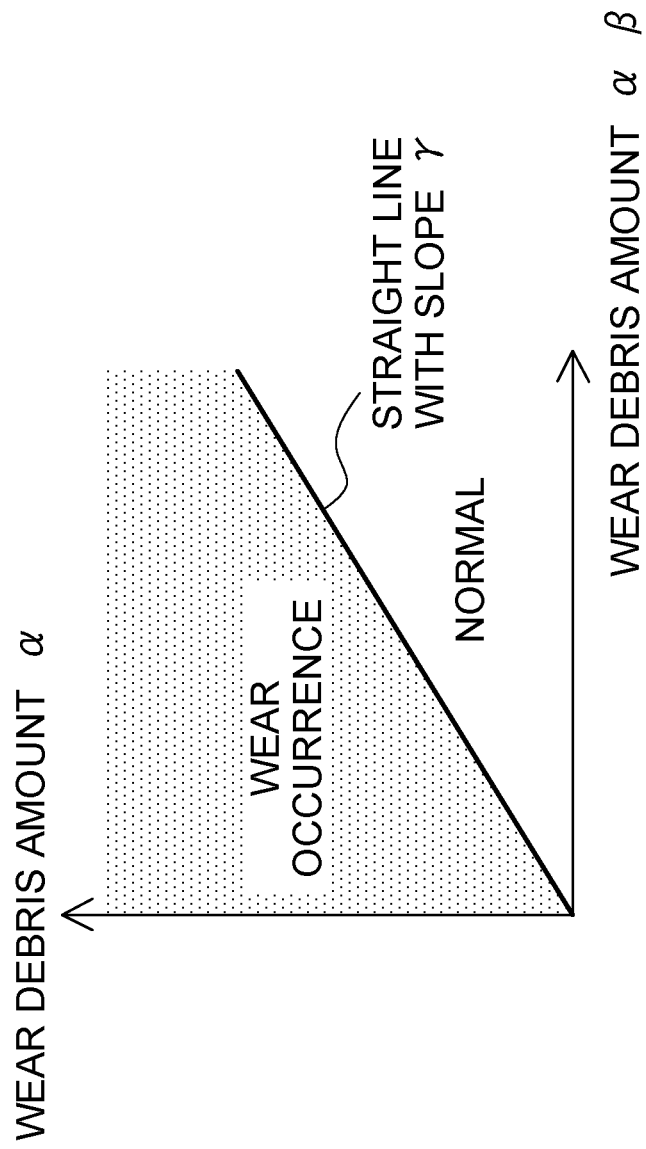
FIG. 4 is a view showing a graph of a relationship between a wear debris amount and a threshold value.

FIG. 4 is a view showing a graph of the relationship between the wear debris amount $\alpha$ and $\beta$, and the threshold value. Here, when bubbles occur, the bubbles pass through the inspection filter 45, so that the detection of bubbles when the bubbles are erroneously detected as wear debris is included in both $\alpha$ and $\beta$.

On the other hand, when the wear debris flows, the wear debris is collected by the inspection filter 45, so that the detection of the wear debris is not included in $\beta$ but included only in $\alpha$.

Therefore, by setting the horizontal axis to the value of $\alpha+\beta$ and the vertical axis to the value of $\alpha$, it is possible to reduce erroneous detection of wear debris due to bubbles. Then, when the value of $\alpha/(\alpha+\beta)$ is equal to or greater than the threshold value $\gamma$, it is determined that wear occurs, and when the value of $\alpha/(\alpha+\beta)$ is smaller than the threshold value $\gamma$, it is determined to be normal.

The memory 54 stores data of the wear debris amount $\alpha$, the wear debris amount $\beta$, the image $\delta$, the bubble determination result, and the wear determination result. Further, the memory 54 stores the predetermined threshold value regarding transparency and the threshold value $\gamma$ regarding the wear debris amount.

The display section 55 displays data of the wear debris amount $\alpha$, the wear debris amount $\beta$, the image $\delta$, the bubble determination result, and the wear determination result.

In the present embodiment, the influence of the bubbles is reduced to detect the occurrence of wear, but when the bubbles occur, the detection accuracy about the occurrence of wear is lowered. Therefore, when the bubble is detected by the bubble determination section 52, the operator who confirms the display section 55 can determine that the value of the wear debris amount α detected by the first contamination sensor 42 and the value of the wear debris amount β detected by the second contamination sensor 43 are low in the inspection accuracy.

When it is determined that bubbles occur or wear occurs, the transmitter 56 transmits a signal indicating the determination result to the work vehicle 1.

The bubble determination section 52 and the wear determination section 53 in the first embodiment can be executed by a processor such as a CPU (Central Processing Unit).

Further, an example of the inspection system for the hydraulic equipment of the first embodiment corresponds to a configuration including the inspection device 20 for the hydraulic equipment, the receiver 51, a bubble determination section 52, and a wear determination section 53.

Operation

Next, the operation of the work vehicle management system of the first embodiment will be described.

Operation of Work Vehicle

Figure 5:
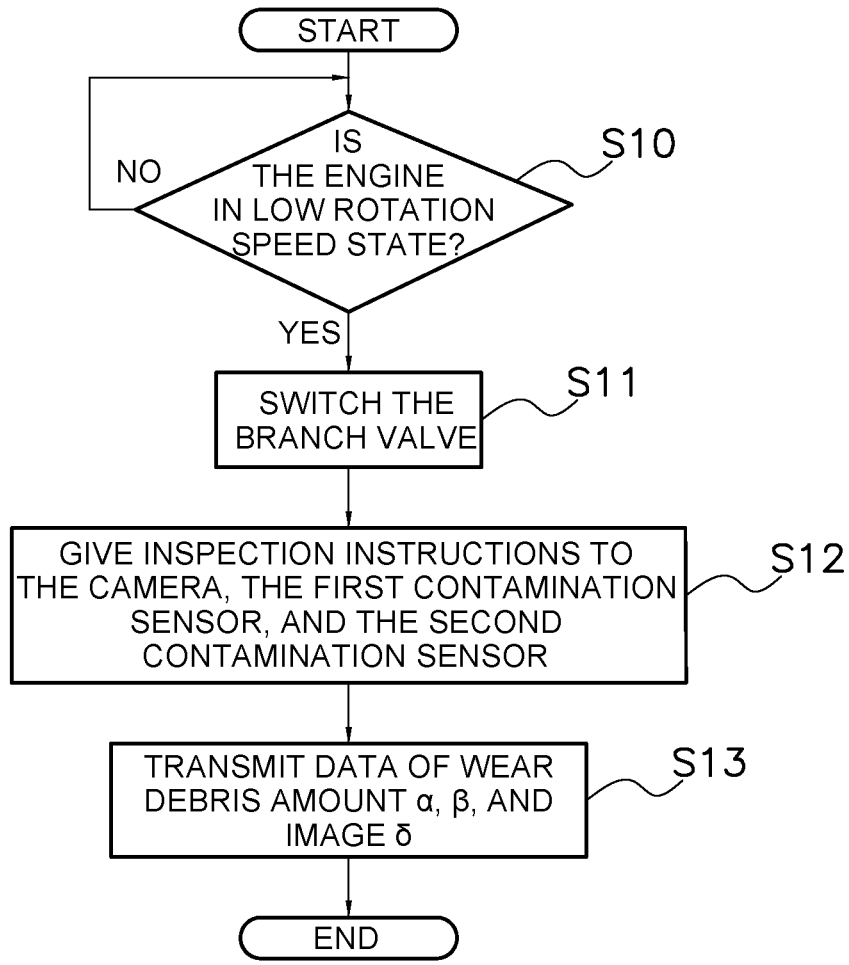
FIG. 5 is a flow chart showing an operation of work vehicle in FIG. 1.

First, the operation of the work vehicle 1 will be described, and an example of the inspection method for the hydraulic equipment of the present invention will be described at the same time. FIG. 5 is a flow chart showing the operation of the work vehicle 1.

When the value of the rotation speed detection sensor 23a becomes lower than the predetermined threshold value in step S10, the controller 25 determines that the engine has reached a low rotation speed state, and the control proceeds to step S11 (an example of the oil supply step).

In step S10, when the value of the rotation speed detection sensor 23a is equal to or higher than the predetermined threshold value, the inspection process for the hydraulic equipment in the work vehicle 1 is in a standby state until the value becomes lower than the predetermined threshold.

In step S11, the controller 25 switches the branch valve 33 to connect the pipeline L1 and the inspection pipeline L11.

Next, in step S12 (an example of a foreign matter detection step), the controller 25 gives inspection instructions to the camera 44, the first contamination sensor 42, and the second contamination sensor 43, and the data of the wear debris amount α, the wear debris amount β, and the image δ are acquired.

Next, in step S13, the transmitter 26 transmits the data of the wear debris amount α, the wear debris amount β, and the image δ to the management device 2.

After the inspection is completed, the branch valve 33 is returned to its original position, and the pipeline L1 and the pipeline L2 are connected.

Operation of Management Device

Figure 6:
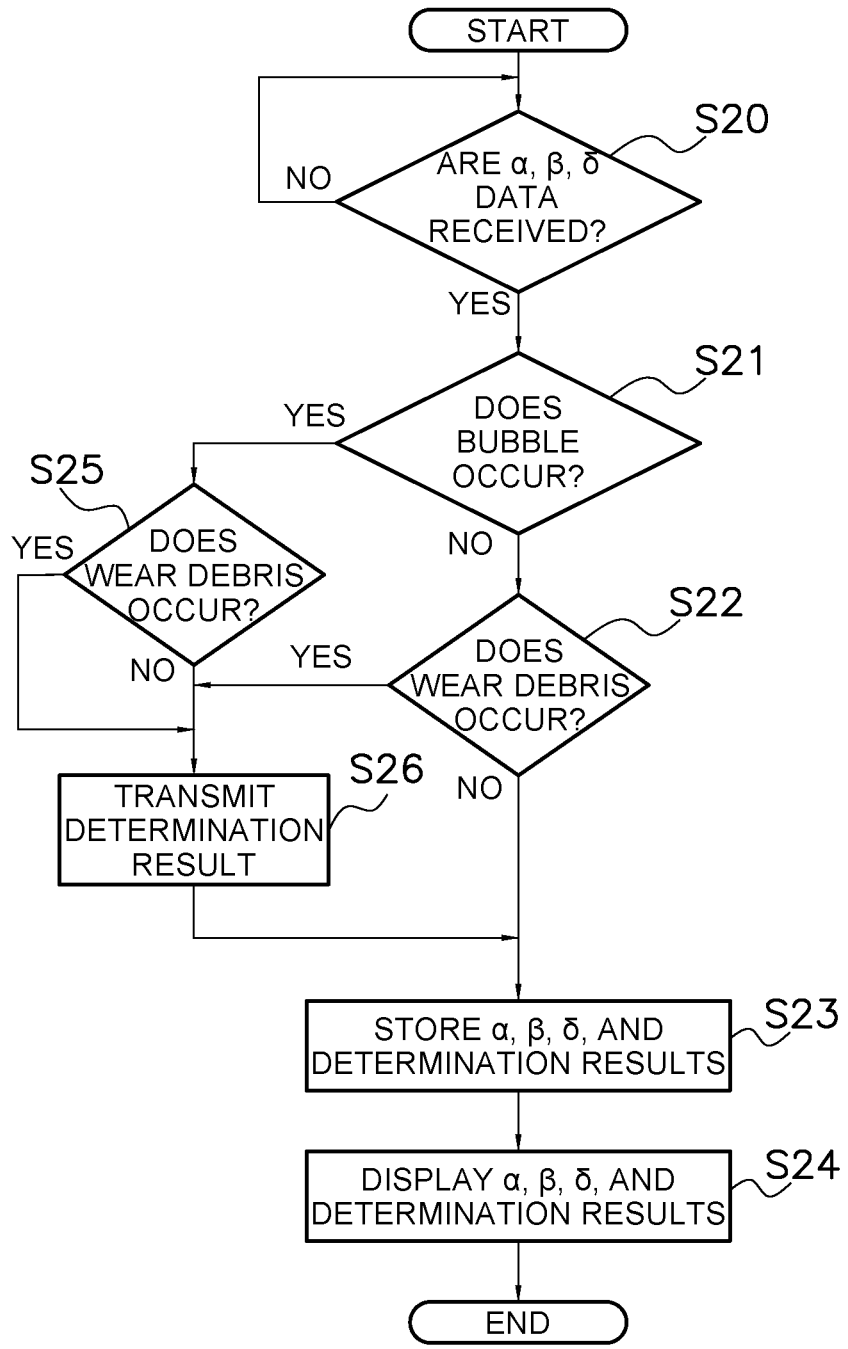
FIG. 6 is a flow chart showing an operation of the management device in FIG. 1.

Next, the operation of the management device 2 will be described. FIG. 6 is a flow chart showing the operation of the management device 2.

In step S20, the receiver 51 receives the data of the wear debris amount α, the wear debris amount β, and the image δ transmitted from work vehicle 1. In step S20, the management device 2 is in a standby state until the data of the wear debris amount α, the wear debris amount β, and the image δ are received.

Next, in step S21, the bubble determination section 52 detects the transparency of the lubricating oil from the image δ, and determines the occurrence of bubbles depending on whether or not the detected transparency is lower than the predetermined threshold value. The bubble determination section 52 determines that bubbles occur when the transparency is lower than the predetermined threshold value, and determines that no bubbles occur when the transparency is equal to or higher than the predetermined threshold value. Here, "no bubbles occur" means that the amount of bubbles that affects the determination accuracy of the wear debris amount does not occur, and the predetermined threshold value also is set a value that does not affect the determination accuracy of the wear debris amount.

When it is determined that no bubbles occur in step S21, the control proceeds to step S22, and the determination about wear is performed.

In step S22, the wear determination section 53 calculates the value of $\alpha/(\alpha+\beta)$ from the data of the wear debris amount α and β, and determines the occurrence of wear depending on whether or not the calculated value is equal to or greater than the predetermined threshold value γ. The wear determination section 53 determines that wear occurs when the value of $\alpha/(\alpha+\beta)$ is equal to or higher than the predetermined threshold value γ, and that no wear occurs when the value of $\alpha/(\alpha+\beta)$ is smaller than the predetermined threshold value γ.

When it is determined that no wear occurs in step S22, the control proceeds to step S23.

In step S23, the data of the wear debris amount α and β, the image δ, the bubble determination result "no occurrence" and the wear determination result "no occurrence" are stored in the memory 54.

Next, in step S24, the data of the wear debris amount α and β, the image δ, the bubble determination result "no occurrence" and the wear determination result "no occurrence" are displayed on the display section 55. It should be noted that the display may be performed only when necessary by the work of the operator.

On the other hand, when it is determined in step S21 that bubbles occur, the control proceeds to step S25, and in step S25, determination about the occurrence of wear is performed. The determination of wear in step S25 is the same as in step S22.

Then, when it is determined in step S25 that wear occurs, in step S26, the transmitter 56 sends a signal indicating the bubble determination result "occurrence" and the wear determination result "occurrence" to work vehicle 1.

When the work vehicle 1 receives the signal indicating the determination result by the receiver 27, the controller 25 turns on the caution lamp 14a provided in the driver's cab 14.

Next, in step S23, the data of the wear debris amount α and β, the image δ, the bubble determination result "occurrence" and the wear determination result "occurrence" are stored in the memory 54.

Next, in step S24, the data of the wear debris amount α and β, the image δ, the bubble determination result "occurrence" and the wear determination result "occurrence" are displayed on the display section 55.

Further, when it is determined in step S25 that no wear occurs, in step S26, the transmitter 56 sends a signal indicating that the bubble determination result "occurrence" and the wear determination result "no occurrence" to the work vehicle 1. When the work vehicle 1 receives the signal indicating the determination result by the receiver 27, the controller 25 turns on the caution lamp 14a provided in the driver's cab 14.

Next, in step S23, the data of the wear debris amount α and β, the image δ, the bubble determination result "occurrence" and the wear determination result "no occurrence" are stored in the memory 54.

Next, in step S24, the data of the wear debris amount α and β, the image δ, the bubble determination result "occurrence" and the wear determination result "no occurrence" are displayed on the display section 55.

Further, when it is determined in step S22 that wear occurs, the control proceeds to step S26, and in step S26, the transmitter 56 sends the a signal indicating that the bubble determination result "no occurrence" and the wear determination result "occurrence" to the work vehicle 1. When the work vehicle 1 receives the signal indicating the determination result by the receiver 27, the controller 25 turns on the caution lamp 14a provided in the driver's cab 14.

Next, in step S23, the data of the wear debris amount α and β, the image δ, the bubble determination result "no occurrence" and the wear determination result "occurrence" are stored in the memory 54.

Next, in step S24, the data of the wear debris amount α and β, the image δ, the bubble determination result "no occurrence" and the wear determination result "occurrence" are displayed on the display section 55.

Embodiment 2

Figure 7:
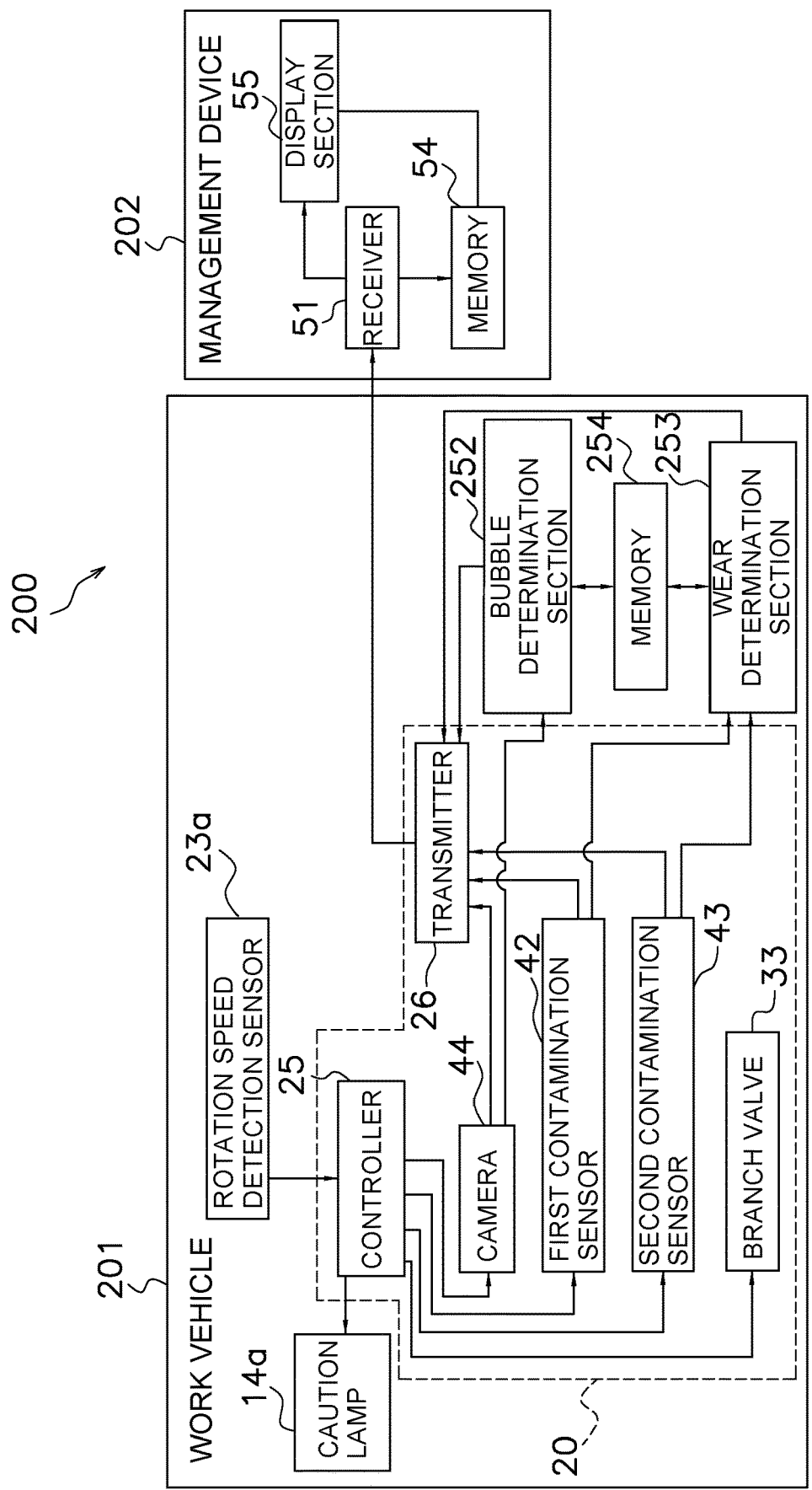
FIG. 7 is a block diagram showing a configuration of a work vehicle management system according to a second embodiment of the present invention.

Next, a work vehicle management system 200 according to the second embodiment of the present invention will be described. In the work vehicle management system 200 according to the second embodiment, bubble determination and wear determination are performed on the work vehicle Configuration FIG. 7 is a block diagram showing the configuration of the work vehicle management system 200. The work vehicle management system 200 includes a work vehicle 201 and a management device 202.

Work Vehicle

The work vehicle 201 in the second embodiment further includes a bubble determination section 252, a wear determination section 253, and a memory 254 in addition to the configuration of the work vehicle 1 in the first embodiment. The work vehicle 201 may not be provided with the receiver 27.

Similar to the bubble determination section 52, the bubble determination section 252 detects the transparency from the data of the image δ, and when the detected transparency is lower than the predetermined threshold value, the bubble determination section 252 determines that bubbles occur.

Similar to the wear determination section 53, the wear determination section 253 determines that wear occurs from the values of the wear debris amount α and the wear debris amount β. Specifically, the wear determination section 253 determines that wear occurs when the value of $\alpha/(\alpha+\beta)$ is equal to or greater than the predetermined threshold value γ.

The memory 254 stores the data of the bubble determination result, the wear determination result, the wear debris amount α, the wear debris amount β, and the image δ. Further, the memory 54 stores a predetermined threshold value regarding transparency and a threshold value γ regarding the wear debris amount.

The transmitter 26 transmits the data of the bubble determination result, the wear determination result, the wear debris amount α, the wear debris amount β, and the image δ to the management device 202.

Further, the controller 25 turns on the caution lamp 14a when the bubble determination section 252 determines that bubbles occur.

The controller 25, the bubble determination section 252, and the wear determination section 253 can be executed by a processor such as a CPU (Central Processing Unit).

Management Device

The management device 202 in the second embodiment does not include the bubble determination section 52, the wear determination section 53, and the transmitter 56 as compared with the management device 2 in the first embodiment.

In the management device 202, the receiver 51 receives the data of the bubble determination result, the wear determination result, the wear debris amount α, the wear debris amount β, and the image δ transmitted from the work vehicle 201.

The memory 54 stores the received data of the bubble determination result, wear determination result, wear debris amount α, wear debris amount β, and image δ.

The display section 55 displays the stored data of bubble determination result, wear determination result, wear debris amount α, wear debris amount β, and image δ.

In the second embodiment, an example of the inspection system for the hydraulic equipment corresponds to a configuration having an inspection device 20 for the hydraulic equipment excluding the transmitter 26, a bubble determination section 252, and a wear determination section 253.

Operation

Next, the work vehicle management system according to the second embodiment will be described.

Operation of Work Vehicle

Hereinafter, work vehicle 201 of the second embodiment will be described, and an example of the inspection method for the hydraulic equipment of the present invention will be described at the same time.

Figure 8:
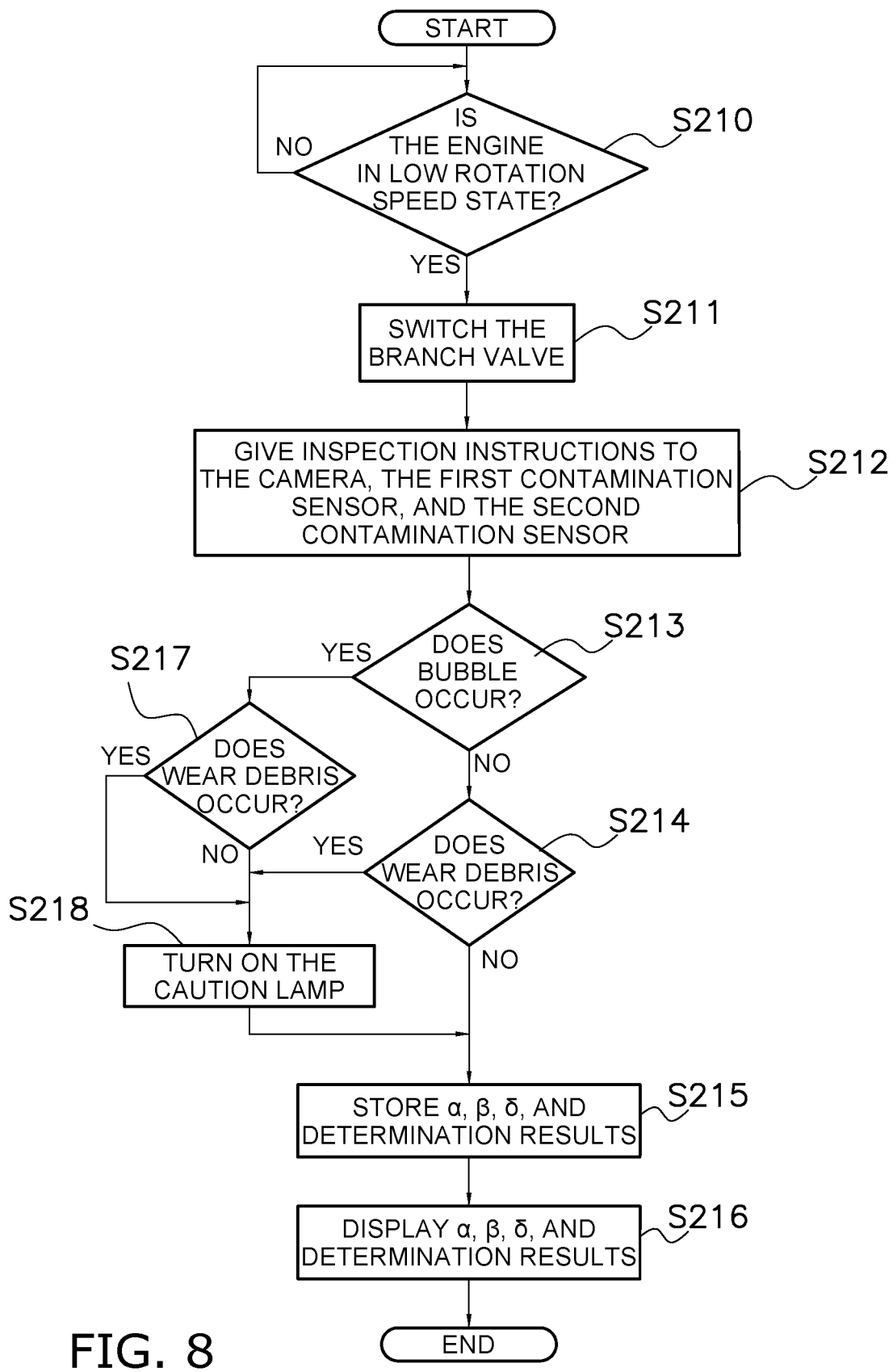
FIG. 8 is a flow chart showing an operation of the work vehicle in FIG. 7.

FIG. 8 is a flow chart showing the operation of the work vehicle 201.

When the value of the rotation speed detection sensor 23a becomes lower than the predetermined threshold value in step S210, the controller 25 determines that the engine has reached a low rotation speed state, and the control proceeds to step S211 (an example of the oil supply step). In step S210, when the value of the rotation speed detection sensor 23a is equal to or higher than the predetermined threshold value, the inspection process for the hydraulic equipment in the work vehicle 201 is in a standby state until the value becomes lower than the predetermined threshold.

In step S211 the controller 25 switches the branch valve 33 to connect the pipeline L1 and the inspection pipeline L11.

Next, in step S212 (an example of a foreign matter detection step), the controller 25 gives inspection instructions to the camera 44, the first contamination sensor 42, and the second contamination sensor 43, and the data of the wear debris amount α, the wear debris amount β, and the image δ are acquired.

Next, in step S213, the bubble determination section 252 detects the transparency of the lubricating oil from the image δ, and determines the occurrence of bubbles depending on whether or not the detected transparency is lower than a predetermined threshold value.

When it is determined in step S213 that no bubbles occur, the control proceeds to step S214, and the determination about wear is performed.

In step S214, the wear determination section 253 calculates the value of $\alpha/(\alpha+\beta)$ from the data of the wear debris amount $\alpha$ and $\beta$, and determines the occurrence of wear depending on whether or not the calculated value is equal to or greater than the predetermined threshold value $\gamma$.

When it is determined in step S214 that no wear occurs, the control proceeds to step S215.

Next, in step S215, the data of the wear debris amount $\alpha$ and $\beta$, the image δ, the bubble determination result "no occurrence" and the wear determination result "no occurrence" are stored in the memory 54.

Next, in step S216, the transmitter 26 transmits the data of the wear debris amount $\alpha$ and $\beta$, the image δ, the bubble determination result "no occurrence" and the wear determination result "no occurrence" to the management device 202.

On the other hand, when it is determined in step S213 that bubbles occur, the control proceeds to step S217, and in step S217, the determination about the occurrence of wear is performed. The determination about wear in step S217 is the same as in step S214.

Then, when it is determined in step S217 that wear occurs, the control proceeds to step S218, and in step S218, the controller 25 turns on the caution lamp 14a.

Next, in step S215, the data of the wear debris amount $\alpha$ and $\beta$, the image δ, the bubble determination result "occurrence" and the wear determination result "occurrence" are stored in the memory 54.

Next, in step S216, the transmitter 26 transmits data of the wear debris amount $\alpha$ and $\beta$, the image δ, the bubble determination result "occurrence" and the wear determination result "occurrence" to the management device 202.

When it is determined in step S217 that no wear occurs, the control proceeds to step S218, and in step S218, the controller 25 turns on the caution lamp 14a.

Next, in step S215, the data of the wear debris amount $\alpha$ and $\beta$, the image δ, the bubble determination result "occurrence" and the wear determination result "no occurrence" are stored in the memory 54.

Next, in step S216, the transmitter 26 transmits the data of the wear debris amount $\alpha$ and $\beta$, the image δ, the bubble determination result "occurrence" and the wear determination result "no occurrence" to the management device 202.

When it is determined in step S214 that wear occurs, the control proceeds to step S218, and in step S218, the controller 25 turns on the caution lamp 14a.

Next, in step S215, the data of the wear debris amount $\alpha$ and $\beta$, the image δ, the bubble determination result "no occurrence" and the wear determination result "occurrence" are stored in the memory 54.

Next, in step S216, the transmitter 26 transmits the data of the wear debris amount $\alpha$ and $\beta$, the image δ, the bubble determination result "no occurrence" and the wear determination result "occurrence" to the management device 202.

Operation of Management Device

Figure 9:
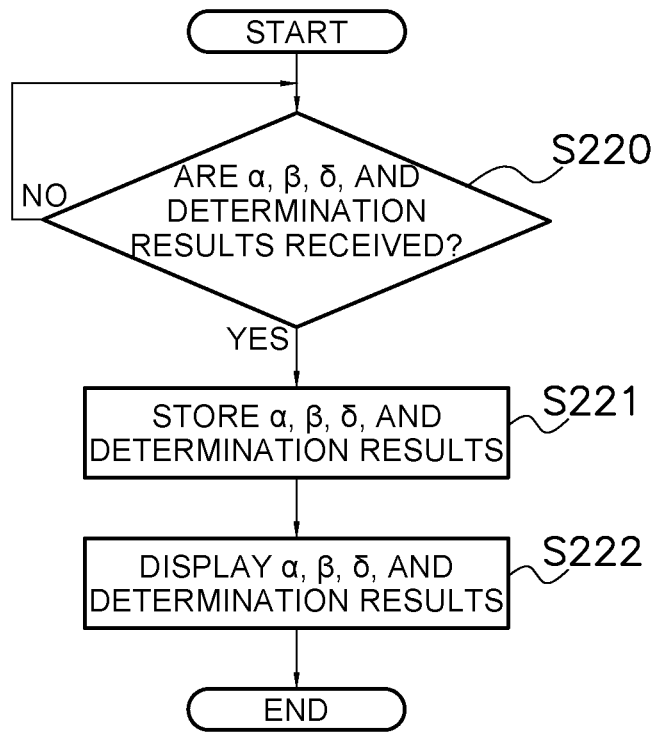
FIG. 9 is a flow chart showing an operation of the management device in FIG. 7.

FIG. 9 is a flow chart showing the operation of the management device 202.

In step S220, the receiver 51 receives the data of the wear debris amount $\alpha$, the amount of wear debris $\beta$, the image δ, the bubble determination result, and the wear determination result transmitted from work vehicle 201. In step S220, the management device 202 is in the standby state until the data of the wear debris amount $\alpha$, the wear debris amount $\beta$, the image δ, the bubble determination result, and the wear determination result are received. The bubble determination result includes the determination result that bubbles occur or no bubble occur, and the wear determination result includes the determination result that wear occurs or no wear occurs.

Next, in step S221, the data of the wear debris amount $\alpha$, the wear debris amount $\beta$, the image δ, the bubble determination result, and the wear determination result are stored in the memory 54.

Next, in step S222, the data of the wear debris amount $\alpha$, the wear debris amount $\beta$, the image δ, the bubble determination result, and the wear determination result are displayed on the display section 55. It should be noted that the display may be performed only when necessary by the work of the operator.

Features, etc.

(1)

The inspection device 20 for the hydraulic equipment of the first and second embodiments includes the hydraulic circuit 21, the optical detection section 24, the hydraulic pump 22, and the controller 25. The hydraulic circuit 21 includes the branch valve 33. The optical detection section 24 has the inspection oil passage 41 which is connected to the branch valve and includes the inspection filter 45 (an example of a filter) for collecting wear debris (an example of a foreign substance). The hydraulic pump 22 supplies oil to the hydraulic circuit 21. The controller 25 operates the branch valve 33 to supply oil to the inspection oil passage 41. The optical detection section 24 includes the first contamination sensor 42 (an example of a first foreign matter detection section) and the second contamination sensor 43 (an example of a second foreign matter detection section). The first contamination sensor 42 is arranged on the upstream side of the inspection filter 45 and detects wear debris. The second contamination sensor 43 is arranged on the downstream side of the inspection filter 45 and detects wear debris.

By arranging the contamination sensors at two locations on the upstream side and the downstream side of the inspection filter 45 in this way, the influence of bubbles can be reduced and wear debris can be detected with high accuracy. That is, the inspection filter 45 collects the wear debris, but since the inspection filter 45 allows bubbles to pass through, both the first contamination sensor 42 and the second contamination sensor 43 erroneously detect the wear debris due to the influence of the bubbles. On the other hand, in the case of wear debris, wear debris is detected only by the first contamination sensor 42.

Therefore, by using the detection result of the first contamination sensor 42 and the detection result of the second contamination sensor 43, the influence of bubbles can be reduced and it is possible to detect the wear debris with high accuracy.

(2)

The inspection device 20 for the hydraulic equipment of the first and second embodiments further includes an engine 23 (an example of a prime mover). The engine 23 drives a hydraulic pump 22 (an example of a pump). When the engine 23 is in a low rotation speed state, the controller 25 supplies oil to the inspection oil passage 41 by operating the branch valve 33, and detects wear debris (an example of foreign matter) using the optical detection section 24.

When the engine 23 is in a low rotation speed state, the flow velocity of the lubricating oil is slow, so that the occurrence of bubbles can be suppressed. Therefore, the wear debris in the lubricating oil can be detected in a state where the influence of bubbles is reduced, so that it is possible to detect the wear debris with high accuracy.

(3)

In the inspection device 20 for the hydraulic equipment of the first and second embodiments, the optical detection section 24 includes a camera 44 (an example of the bubble detection section). The camera 44 is arranged on the downstream side of the inspection filter 45, and detects bubbles contained in the oil after passing through the inspection filter 45 in order to acquire data regarding the detection accuracy.

Even when the wear debris is detected in the state where the influence of bubbles is reduced as much as possible, an error is likely to occur in the detection result in the case that bubbles occur. Therefore, it is possible to determine whether or not the accuracy of the wear debris detection result is good based on the occurrence of bubbles.

(4)

The inspection device 20 for the hydraulic equipment of the first and second embodiments further includes a transmitter 26. The transmitter 26 transmits the wear debris amount $\alpha$ and the wear debris amount $\beta$ (an example of data regarding the amount of foreign matter) and the image $\delta$ (an example of data regarding the detection accuracy) to the outside.

As a result, the state of the work vehicle 1 can be determined in the external management device 2. For example, the management device 2 can determine whether or not the wear debris is flowing in the lubricating oil from the wear debris amount $\alpha$ and the wear debris amount $\beta$. Further, from the image $\delta$, it can be determined whether or not bubbles occur in the lubricating oil during the inspection of the wear debris.

Then, if necessary, it is possible to turn on the caution lamp 14a in the work vehicle 1 or to contact the operator.

(5)

The work vehicles 1 and 201 in the first and second embodiments are provided with an inspection device 20 for hydraulic equipment, and the hydraulic circuit 21 includes the transmission 37 having a gear.

As a result, it is possible to accurately detect whether or not the lubricating oil supplied to the transmission 37 contains wear debris.

(6)

The inspection system for hydraulic equipment according to the first and second embodiments includes an inspection device 20 for the hydraulic equipment, the wear determination section 53 or 253 (an example of a foreign matter determination section), and the bubble determination section 52 or 252. The wear determination section 53 or 253 determine wear debris (an example of a foreign matter) based on the detection results of the first contamination sensor 42 (an example of a first foreign matter detection section) and the second contamination sensor 43 (an example of a second foreign matter detection section). The bubble determination sections 52 or 252 determine bubbles based on the detection results of the camera 44 (an example of the bubble detection section).

Thereby, it is possible to determine bubbles and wear debris.

(7)

The inspection method for the hydraulic equipment in the first and second embodiments includes steps S11 or S211 (an example of an oil supply step) and step S12 or S212 (an example of a foreign matter detection step). Step S1 or step S211 includes supplying oil to the inspection oil passage 41 by operating the branch valve 33 arranged on a hydraulic circuit 21. Step S12 or step S212 includes detecting wear debris (an example of foreign matter) on both the upstream side and the downstream side of the inspection filter 45 (an example of a filter) arranged on the inspection oil passage 41.

In this way, by detecting the wear debris at two locations on the upstream side and the downstream side of the inspection filter 45, the influence of bubbles can be reduced and it is possible to detect the wear debris with high accuracy.

(8)

In the inspection method for the hydraulic equipment of the first and second embodiments, step S11 or step S211 (an example of an oil supply step) includes supplying oil to the inspection oil passage 41 by operating the branch valve 33 when the engine 23 (an example of a prime mover) that drives a hydraulic pump 22 for supplying oil to the hydraulic circuit 21 is in a low rotation speed state.

When the engine 23 is in a low rotation speed state, the flow velocity of the lubricating oil is slow, so that the generation of bubbles can be suppressed. Therefore, the wear debris in the lubricating oil can be detected in a state where the influence of bubbles is reduced, so that it is possible to detect the wear debris with high accuracy.

(9)

In the inspection method for the hydraulic equipment of the first and second embodiments, step S12 or step S212 includes detecting bubbles contained in the oil supplied to the inspection oil passage 41 in order to acquire data regarding the detection accuracy.

Even when the wear debris is detected in the state where the influence of bubbles is reduced as much as possible, an error is likely to occur in the detection result in the case that bubbles occur. Therefore, it is possible to determine whether or not the accuracy of the wear debris detection result is good based on the occurrence of bubbles.

(10)

The inspection method for the hydraulic equipment of the first and second embodiments further includes step S13 (an example of a transmission step). Step S13 includes transmitting the wear debris amount $\alpha$ and $\beta$ (an example of data relating to the amount of foreign matter) and the image $\delta$ (an example of data relating to the detection accuracy) to the outside.

As a result, the state of the work vehicle 1 can be determined in the external management device 2. For example, the management device 2 can determine whether or not the wear debris is flowing in the lubricating oil from the wear debris amount $\alpha$ and the wear debris amount $\beta$. Further, from the image $\delta$, it can be determined whether or not bubbles occur in the lubricating oil during the inspection of the wear debris.

Other Embodiments

Although one embodiment of the present invention has been described above, the present invention is not limited to the above embodiment, and various modifications can be made without departing from the gist of the invention.

(A)

In the first and second embodiments, the second contamination sensor 43 detects the wear debris amount in the lubricating oil flowing through the pipeline L2, but it is not limited to this, and the wear debris amount in the lubricating oil flowing through the inspection pipeline L12 may be detected.

(B)

In the first and second embodiments, the camera 44 captures the image of the pipeline L2 on the downstream side of the inspection filter 45, but not limited the pipeline L2, the camera 44 may captures the inspection pipeline L12. Since the inspection filter 45 allow bubbles to pass through, the camera 44 may capture the inspection pipeline L11.

(C)

In the first and second embodiments, when the engine 23 is in a low rotation speed state, the flow path of the branch valve 33 is completely switched from the pipeline L2 to the inspection pipeline L11, but the present invention is not limited to this. For example, only a part of the lubricating oil supplied to the pipeline L2 may be controlled to flow to the inspection pipeline L11.

(D)

In the embodiments, the caution lamp 14a is turned on when either the occurrence of bubbles or the occurrence of wear is detected, but the caution lamp 14a may be turned on only when either one is detected. For example, the caution lamp 14a may be turned on only when the bubble determination section 52 determines that bubbles occur.

Further, lamps may be provided separately for the occurrence of bubbles and the occurrence of wear.

(E)

The work vehicle 201 in the second embodiment includes both the bubble determination section 52 and the wear determination section 53, but only one of them may be provided. In that case, it is preferable that the management device 202 includes one that the work vehicle 201 does not include.

(F)

In the second embodiment, since the work vehicle 201 performs the bubble determination and the wear determination, the transmitter 26 may not be provided in the inspection device 20 for the hydraulic equipment when the management device 202 does not manage the bubble determination and the wear determination.

(G)

In the first and second embodiments, the controller 25 determines that the engine 23 is in a low rotation speed state when the rotation speed of the engine 23 is equal to or less than the predetermined rotation speed, but the controller 25 may determine that the engine 23 is in a low rotation speed state when the rotation speed of the engine 23 is continuously equal to or lower than the predetermined speed for a predetermined time or longer.

(H)

In the first and second embodiments, it is determined that the engine 23 is in the low rotation speed state by detecting the rotation speed of the engine 23, but it may be determined that the engine 23 is in the low rotation speed state by detecting that the parking brake is operated, and the controller 25 may give a switching instruction to the branch valve 33.

(I)

In the above-described first and second embodiments, the explanation was given a bulldozer as an example of the work vehicle 1 and 201, but the present invention is not limited to this, and a wheel loader, a dump truck, a grader, or the like may be used as an example of the work vehicles 1 and 201.

(J)

In the first and second embodiments, the system for inspecting foreign matter in the lubricating oil supplied to the transmission 37 as the inspection device 20 for the hydraulic equipment has been described as an example, but the present invention is not limited to this, and the present invention can be applied as long as a configuration supplies hydraulic oil or lubricating oil to the hydraulic equipment.

The inspection device for hydraulic equipment of the present invention has an effect of being able to accurately inspect foreign matter mixed in the hydraulic circuit, and is useful as work vehicle

The invention claimed is:

1. An inspection device for a hydraulic equipment, the inspection device comprising:
   a hydraulic circuit including a branch valve;
   an optical detection section including an inspection oil passage connected to the branch valve, the inspection oil passage including a filter arranged to collect foreign matter;
   a pump configured to supply oil to the hydraulic circuit; and
   a controller configured to operate the branch valve to supply oil to the inspection oil passage upon determining that a foreign matter inspection will be performed, the branch valve being operated from a state in which the branch valve stops the oil from being supplied to the inspection oil passage,
   the optical detection section including
      a first foreign matter detection section arranged on an upstream side of the filter, the first foreign matter detection section being configured to detect foreign matter,
      a second foreign matter detection section arranged on a downstream side of the filter, the second foreign matter detection section being configured to detect foreign matter, and
      a bubble detection section arranged on a downstream side of the filter, the bubble detection section being configured to detect a bubble contained in oil after the oil has passed through the filter in order to acquire data regarding detection accuracy,
   the inspection oil passage being disposed on an upstream side of the pump and configured to branch from the hydraulic circuit via the branch valve and merge back with the hydraulic circuit, and
   the bubble detection section being arranged between the filter and the pump.

2. The inspection device for the hydraulic equipment according to claim 1, further comprising:
   a prime mover configured to drive the pump,
   the controller being configured to
      determine whether the prime mover is in a low rotational speed state,
      determine that the foreign matter inspection will be performed upon determining that the prime mover is in the low rotation speed state, and
      detect whether foreign matter exists using the optical detection section upon determining that the foreign matter inspection will be performed.

3. The inspection device for the hydraulic equipment according to claim 1, further comprising:
   a transmitter configured to transmit
      data regarding an amount of foreign matter to an outside and
      data regarding the detection accuracy to the outside.

4. A work vehicle including the inspection device for the hydraulic equipment according to claim 1, wherein
the hydraulic circuit includes a transmission having gears.

5. An inspection system for the hydraulic equipment including the inspection device for the hydraulic equipment according to claim 1, the inspection system further comprising:
a foreign matter determination section configured to determine foreign matter based on detection results of the first foreign matter detection section and the second foreign matter detection section; and
a bubble determination section configured to determine a bubble based on a detection result of the bubble detection section.

6. The inspection device for the hydraulic equipment according to claim 1, wherein
the bubble detection section is a camera.

7. The inspection device for the hydraulic equipment according to claim 1,
the branch valve and the inspection oil passage are disposed on a suction side of the pump.

8. The inspection device for the hydraulic equipment according to claim 1,
an upstream end of the inspection oil passage is connected to the branch valve,
a downstream end of the inspection oil passage is connected to a suction passage, the suction passage being connected to a suction side of the pump, and
the branch valve is configured and arranged to switch between a first state in which the oil flows from the branch valve into the suction passage without passing through the inspection oil passage and a second state in which the oil flows from the branch valve into the inspection oil passage.

9. An inspection method for a hydraulic equipment, the inspection method comprising:
supplying oil to an inspection oil passage by operating a branch valve arranged in a hydraulic circuit upon determining that a foreign matter inspection will be performed, the operating the branch valve being executed from a state in which the branch valve stops the oil from being supplied to the inspection oil passage; and
detecting foreign matter on both an upstream side and a downstream side of a filter arranged in the inspection oil passage upon determining that the foreign matter inspection will be performed,
the inspection oil passage being disposed on an upstream side of the pump and configured to branch from the hydraulic circuit via the branch valve and merge back with the hydraulic circuit, and
the detecting foreign matter including detecting a bubble contained in oil supplied to the inspection oil passage in order to acquire data regarding detection accuracy, the detecting the bubble being performed at a location between the filter and the pump.

10. The inspection method for the hydraulic equipment according to claim 9, further comprising
determining whether a prime mover configured to drive a pump is in a low rotational speed state, the pump being configured to supply oil to the hydraulic circuit,
determining that the foreign matter inspection will be performed upon determining that the prime mover is in the low rotation speed state.

11. The inspection method for the hydraulic equipment according to claim 7, wherein
the detecting foreign matter includes detecting a bubble contained in oil supplied to the inspection oil passage in order to acquire data regarding detection accuracy.

12. The inspection method for the hydraulic equipment according to claim 9, further comprising:
transmitting
data regarding an amount of foreign matter to an outside and
data regarding the detection accuracy to the outside.

13. The inspection method for the hydraulic equipment according to claim 9, wherein
the operating the branch valve includes switching the branch valve from a first state in which the oil flows from the branch valve to the pump without passing through the inspection oil passage to a second state in which the oil flows from the branch valve into the inspection oil passage.

* * * * *